United States Patent [19]

Collignon

[11] Patent Number: 4,894,462

[45] Date of Patent: Jan. 16, 1990

[54] PREPARATION OF SPHEROIDAL 3-NITRO-1,2, 4-TRIAZOLE-5-ONE

[75] Inventor: Steven L. Collignon, Waldorf, Md.

[73] Assignee: The United States of America as represented by the Secretary of the Navy, Washington, D.C.

[21] Appl. No.: 213,037

[22] Filed: Jun. 24, 1988

[51] Int. Cl.$^4$ ............................................. C07D 249/12
[52] U.S. Cl. ..................................... 548/265; 548/263
[58] Field of Search ................................ 548/263, 265

[56] References Cited

U.S. PATENT DOCUMENTS 4,733,610  3/1988  Lee et al. ............................. 548/263

Primary Examiner—Donald G. Dauss
Attorney, Agent, or Firm—Kenneth E. Walden; Roger D. Johnson

[57] ABSTRACT

A process for recrystallizing crude, rod-like or jagged crystals of 3-nitro-1,2,4-triazol-5-one into spheroidal crystals by using low molecular weight alcohols (e.g., methanol, ethanol).

6 Claims, No Drawings

PREPARATION OF SPHEROIDAL 3-NITRO-1,2,4-TRIAZOLE-5-ONE

BACKGROUND OF THE INVENTION

This invention relates to heterocylic organic explosives and more particularly to nitrated triazoles.

3-nitro-1,2,4-triazol-5-one (NTO) is typically recrystallized in water. Unfortunately, NTO recrystallizes from water in jagged rod-like particles that have a tendency to agglomerate. The irregular and jagged crystal shapes causes the mixing of the explosive formulations with NTO to be highly viscous and difficult to process and to pour. As a result, the amount of NTO which can be used in a processable explosive composition is limited and the performance of the explosive is therefor reduced.

SUMMARY OF THE INVENTION

Accordingly an object of this invention is to provide a method of converting jagged rod-like 3-nitro-1,2,4-triazol-5-one crystals into spheroidal crystals.

Another object of this invention is to provide an inexpensive method of producing spheroidal crystals of 3-nitro-1,2,4-triazol-5-one.

These and other objects of this invention are accomplished by providing:
a process comprising the following steps in order:
(1) completely dissolving 3-nitro-1,2,4-triazol-5-one in a low molecular weight alcohol of from 1 to 5 carbon atoms at a temperature of from 40° C. up to just below the boiling point of the alcohol at ambient pressure;
(2) cooling the 3-nitro-1,2,4-triazol-5-one/alcohol solution at a rate of from 6° C./minute to 20° C./minute while the solution is agitated until the solution is at a temperature in the range of from −10° C. to +5° C.; and
(3) isolating the product spheroidal crystals of 3-nitro-1,2,4-triazol-5-one.

DETAILED DESCRIPTION OF THE PREFERRED EMBODIMENT

This invention is based on the surprising discovery that 3-nitro-1,2,4-triazol-5-one crystallizes from lower molecular weight alcohols in the form of spheroidal crystals rather than as jagged needles. Conventionally, 3-nitro-1,2,4-triazol-5-one has been crystallized from water in the form of jagged needles.

Lower molecular weight alcohols of from 1 to 5 carbon atoms may be used. However, methanol and ethanol are preferred because of their low costs. Ethanol is more preferred than methanol because methanol is toxic. Further, ethanol, because of its higher boiling point, will dissolve more 3-nitro-1,2,4-triazol-5-one than methanol will.

Alcohols containing as much as 10 percent water (as an impurity) by weight will produce the spheroidal crystals. Thus, inexpensive commercial grades of alcohols which contain some water may be used. For example, commercial grade ethanol containing 5% water works well in this process. In summary, alcohol as defined in this process includes a mixture of the alcohol and up to 10 percent by weight water.

In the first step of this process, crude jagged rod-like 3-nitro-1,2,4-triazol-5-one is dissolved in the alcohol at a temperature of from 40° C. to just below the boiling point of the alcohol and more preferably from 60° C. to just below the boiling point of the alcohol at ambient pressure. For example, for methanol this temperature range will be from 40° C. to 62° C. and more preferably from 60° C. to 62° C. For ethanol this temperature range will be from 40° C. to 78° C. and more preferably from 60° C. to 78° C.

Care is taken to assure that all of the crude 3-nitro-1,2,4-triazol-5-one is dissolved. Even small amounts of crude rod-like 3-nitro-1,2,4-triazol-5-one can act as seed crystals causing formation of rod-like crystals rather than the desired spheroidal crystals. This is avoided by using less 3-nitro-1,2,4-triazol-5-one than the amount needed to form a saturated solution and by heating the solution for a sufficient time.

In the second step, the 3-nitro-1,2,4-triazole-5-one/alcohol solution is cooled down to a temperature in the range of from −10° C. to +5° C. at a rate of from 6° C./minute to 20° C./minute. During the cool down, the solution is agitated (e.g., stirred) at a moderate to fast rate. As crystals are formed, the agitation causes them to collide with each other and with parts of the crystallizer (especially the agitator) thus breaking off new crystal nuclei. As is known in the art, this formation of secondary crystal nuclei helps the crystallization process.

Finally, the spheroidal 3-nitro-1,2,4-triazol-5-one crystals are collected (e.g., by filtration) and dried. The alcohol filtrate can be reused in the process.

A significant cost advantage to this process is that no crystal habit modifiers are added to the alcohol solutions.

The general nature of the invention having been set forth, the following examples are presented as specific illustrations thereof. It will be understood that the invention is not limited to these specific examples but is susceptible to various modifications that will be recognized by one of ordinary skill in the art.

EXAMPLE 1

To a 300 ml three-neck flask, 200 g of ethanol and 12.8 g of 3-nitro-1,2,4-triazol-5-one were added. The mixture was heated at 70° C. until the 3-nitro-1,2,4-triazol-5-one had completely dissolved. With agitation (stirring), the solution was cooled with an ice bath to below 5° C. The average cooling rate was approximately 7° C./minute. The product was separated by filtration and dried. The product was white spheroidal crystals of 3-nitro-1,2,4-triazol-5-one.

EXAMPLE 2

The procedure of Example 1 was repeated except that 14.7 g of 3-nitro-1,2,4-triazol-5-one was added and the ethanol was heated to 78° C. Again the product was white spheroidal crystals of 3-nitro-1,2,4-triazol-5-one.

EXAMPLE 3

To a 300 ml three neck flask, 14.7 g of 3-nitro-1,2,4-triazol-5-one, 180 g of ethanol, and 20 g of water were added. The mixture was heated to 65° C. until the 3-nitro-1,2,4-triazol-5-one had dissolved, with agitation the solution was cooled with an ice bath to below 5° C. The average cooling rate was approximately 7° C./minute. The product was separated by filtration and dried. Again, the product was white spheroidal crystals of 3-nitro-1,2,4-triazol-5-one.

Obviously, numerous modifications and variations of the present invention are possible in light of the above teachings. It is therefore to be understood that within the scope of the appended claims the invention may be practiced otherwise than as specifically described herein.

What is claimed is:

1. A process for producing spheroidal crystals of 3-nitro-1,2,4-triazol-5-one comprising the following steps in order:
   (1) completely dissolving 3-nitro-1,2,4-triazol-5-one in a low molecular weight alcohol of from 1 to 5 carbon atoms at a temperature of from 40° C. up to just below the boiling point of the alcohol at ambient pressure;
   (2) cooling the 3-nitro-1,2,4-triazol-one/alcohol solution at a rate of from 6° C./minute to 20° C./minute while the solution is agitated until the solution is at a temperature in the range of from −10° C. to +5° C.; and
   (3) isolating the product spheroidal crystals of 3-nitro-1,2,4-triazol-5-one.

2. The process of claim 1 wherein the temperature used in step (1) is from 60° C. up to just under the boiling point of the alcohol at ambient pressure.

3. The process of claim 1 wherein the alcohol is ethanol and the temperature range in step (1) is from 40° C. to 78° C.

4. The process of claim 3 wherein the temperature range in step (1) is from 60° C. to 78° C.

5. The process of claim 1 wherein the alcohol is methanol and the temperature range in step (1) is from 40° C. to 62° C.

6. The process of claim 5 wherein the temperature range in step (1) is from 60° C. to 62° C.

* * * * *